United States Patent [19]

Neirinckx

[11] 4,400,358

[45] Aug. 23, 1983

[54] METHOD AND ADSORBANT COMPOSITION FOR $^{82}$RB GENERATION

[75] Inventor: Rudi D. Neirinckx, East Windsor, N.J.

[73] Assignee: E. R. Squibb & Sons, Inc., Princeton, N.J.

[21] Appl. No.: 208,918

[22] Filed: Nov. 21, 1980

Related U.S. Application Data

[63] Continuation-in-part of Ser. No. 162,858, Jun. 25, 1980, abandoned.

[51] Int. Cl.[3] .................... C01G 19/02; A61K 43/00; A61K 49/00

[52] U.S. Cl. .................................... 423/2; 252/645; 250/432 PD; 424/1; 422/61

[58] Field of Search ................ 252/645; 423/2; 424/1; 250/432 PD; 422/61

[56] References Cited

U.S. PATENT DOCUMENTS 3,953,567 4/1976 Grant et al. .............................. 423/2

4,276,267 6/1981 Bentley et al. .......................... 423/2

OTHER PUBLICATIONS

Yano et al., J. Nucl. Med. 20 961-966, 1979.

Loc'h et al., J. Nucl. Med. 21:171-173, 1980.

Arino et al., Int. J. Appl. Radiat. Isot. 29:117-120, 1978.

Kopecky et al., Int. J. Appl. Radiat. Isot. 25:263-268.

Neirinckx et al., Second International Symposium on Radio-Pharmaceutical Chemistry, MRC, Oxford, 1978, p. 109.

*Primary Examiner*—Christine M. Nucker

*Attorney, Agent, or Firm*—Lawrence S. Levinson

[57] ABSTRACT

A composition comprising $^{82}$Sr and an adsorbant selected from the group consisting of tin oxide, hydrated tin oxide, polyantimonic acid, titanium oxide, and ferric oxide.

A low $^{82}$Sr breakthrough method of generating $^{82}$Rb from a $^{82}$Sr charged adsorbant comprising eluting wherein said adsorbant is selected from the group consisting of tin oxide, polyantimonic acid, titanium oxide, ferric oxide, and hydrated tin oxide.

13 Claims, No Drawings

METHOD AND ADSORBANT COMPOSITION FOR $^{82}$RB GENERATION

This application is a continuation-in-part of application Ser. No. 162,858 filed June 25, 1980 abandoned.

BACKGROUND OF THE INVENTION

Rubidium-82, a positron emitter with a half-life of 75-sec readily obtainable from the parent Sr-82 ($T_{\frac{1}{2}}=25$ days). Rubidium can be used as a diffusible flow tracer for the myocardium and kidney, and as a nondiffusible tracer for brain blood flow. Serial injections of Rb-82 can be administered every 5 to 10 minutes by eluting (milking) Rb-82 from its 25-day Sr-82 parent. The advantages of Rb-82 are low radiation dose, ability to provide for repeated examinations every 5 minutes without constraints from body background, and a convenient and economical supply of a short-half-life positron emitter. (Yano et al., The Journal of Nuclear Medicine 20:961-966, 1979.)

Significant quantities of $^{82}$Sr are available for clinical investigation. The short-lived daughter, 75-second $^{82}$Rb, is a value in biomedicine for circulation and perfusion studies as well as for myocardial imaging as mentioned in U.S. Pat. No. 3,953,567.

Loc[h et al. J. Nucl. Med. 21: 171-173, 1980 disclose a tin dioxide ($SnO_2$)/HCl Ga-68 generator.

Arino et al. Int. J. Appl. Radiat. Isot. 29: 117-120, 1978 disclose a $^{68}$Ge/$^{68}$Ga radioisotope generator system which uses polyantimonic acid to selectively adsorb Ge and not Ga. The adsorption was speculated to be due to a dehydration reaction forming chemical bonding between Sb and Ge through oxygen.

Neirinckx et al. disclose titanium oxide in a generator for ionic gallium-68, see second International Symposium on Radiopharmaceutical Chemistry MRC. Oxford, 1978, p. 109.

Kopecky et al. Int. J. Appl. Radiat. Isot. 25: 263-268, 1974 disclose a $^{68}$Ge/$^{68}$Ga generator for the production of $^{68}$Ga in an ionic form. Aspects of the adsorption of carrier-free $^{68}$Ge and $^{68}$Ga on alumia, $Al(OH)_3$ and $Fe(OH)_3$ are discussed.

SUMMARY OF THE INVENTION

A composition comprising $^{82}$Sr and an adsorbant selected from the group consisting of tin oxide, hydrated tin oxide, polyantimonic acid, and titanium oxide.

A low $^{82}$Sr breakthrough method of generating $^{82}$Rb from a $^{82}$Sr charged adsorbant comprising eluting the $^{82}$Rb from said adsorbant with an eluant solution wherein said adsorbant is selected from the group consisting of hydrated, unhydrated and mixtures of the hydrated and unhydrated forms of tin oxide, titanium oxide and ferric oxide; and unhydrated polyantimonic acid. The eluant can be physiological saline or a buffered isotonic solution. The yields of $^{82}$Rb are high.

DETAILED DESCRIPTION OF THE INVENTION

Hydrated tin oxide includes hydrated stannic oxide, hydrated stannous oxide, and mixtures of hydrated stannic oxide and hydrated stannous oxide. Preferably the hydrated tin oxide is amorphous.

Tin oxide includes stannic oxide, stannous oxide and mixtures of stannous oxide and stannic oxide.

Most preferably an amorphous mixture comprising tin oxide and a substantial amount (more than 10% by weight) of hydrated stannic oxide is used as the adsorbant.

The method and compositions of the present invention are useful in positron imaging and in the subsequent measurement of blood flow through the myocardium, brain and kidneys.

The present invention provides improved breakthrough characteristics. It has been discovered that breakthrough of Sr may be lowered by providing an adsorbant which is preferably polyantimonic acid, titanium oxide (hydrated), ferric oxide (hydrated), hydrated tin oxide or tin oxide.

The present invention provides a small bolus size of 2-3 ml which is advantageous for lower volume per unit time infusion while maintaining an effective amount of activity to monitor the patient.

Preferably the eluant is isotonic saline or isotonic saline buffered at physiological pH. Preferably a buffered eluant is used and the buffer is a phosphate salt or a carbonate salt. Preferably the buffer is a phosphate salt. Most preferably isotonic saline at physiological pH is used.

Bacteriostats may be beneficially added to the eluant. Preferred bacteriostats are those which are pharmaceutically acceptable buffers, for example parabens.

Infusion speeds of 5-10 ml per minute or higher are useful when using the compositions and method of the present invention.

$^{82}$Rb yields of 90% of theoretical maximum are obtained using the present invention. These yields may be obtained over a 0.1 minute interval using an eluant flow rate of 30 ml/min.

Low $^{82}$Sr breakthroughs of $10^{-9}$/ml are obtained using the present invention.

Beneficially, the present invention provides high yields of $^{82}$Rb with physiological saline as eluant and high radioactive concentration in the eluate (90% elution yield in 5-10 cc).

The eluant may be buffered at a pharmaceutically acceptable pH. Preferably the pH is from 6.0 to Ph 10. Most preferably the pH is from pH 7.0 to pH 7.5 The concentration of the buffer in the eluent preferably is from 0.01 mmol to 200 mmol per liter of eluant solution.

The saline concentration of the eluant is a pharmaceutically acceptable concentration. Preferably the saline is isotonic (0.9%).

A column containing adsorbant is charged with $^{82}$Sr. Preferably the adsorbant is hydrated tin oxide or polyantimonic acid. Most preferably the adsorbant is hydrated tin oxide. The column is then eluted with the eluant.

At clinically useful flow rates of about 20 ml per minute, $^{82}$Sr breakthroughs of $10^{-9}$ per ml of eluant are obtained by the present invention. Breakthrough is the ratio of microcuries of $^{82}$Sr in the eluant to the microcuries of $^{82}$Sr on the adsorber.

Phosphate salts include alkali phosphates, alkaline earth phosphates, alkali metal hydrogen phosphates, alkaline earth hydrogen phosphates as well as hydrates of phosphate salts. Also phosphate salts include all phosphorous oxides which form phosphates upon addition to water.

A preferred phosphate salt is $Na_2HPO_4$ which may be added to the eluant as $Na_2HPO_4.7H_2O$. In the saline eluant it forms $Na+$ and $PO_4^{-3} \rightleftarrows HPO_4^{-2} \rightleftarrows H_2PO_4^{\ominus}$. Upon addition of NaOH some of the $H_2PO_4^{\ominus}$ would be used up in the formation of $HPO_4^{-2}$. The balanced equation being:

$$NaH_2PO_4 + NaOH \rightleftharpoons Na_2HPO_4 + H_2O.$$

When acid is added, for example HCl, some $H_2PO_4^{\ominus}$ is formed. The balanced equation is:

$$Na_2HPO_4 + HCl \rightleftharpoons NaH_2PO_4 + NaCl.$$

Carbonate salts include water soluble carbonate salts such as alkali metal carbonates and alkali metal hydrogen carbonates for example $NaHCO_3$. In water $NaHCO_3$ forms $Na^+$ and $CO_3^{-2} \rightleftharpoons H\,CO_3^{\ominus} \rightleftharpoons H_2CO_3$. Upon addition of NaOH; $HCO_3^{-1}$ and $H_2CO_3$ are used up and $CO_3^{-2}$ and $HCO_3^{-1}$ respectively are formed. Upon addition of HCl; $CO_3^{-2}$ and $HCO_3^-$ are used up and $HCO_3^-$ and $H_2CO_3$ respectively are formed.

The procedure used in examples 1-4 is as follows:

50 mg amounts of one of $Ti(OH)_4$, polyantimonic acid. $SnO_2$ (hydrated) or ferric oxide are shaken with 5 ml of liquid phase. The liquid phase is either isotonic saline (0.9% NaCl) or saline and phosphate salt solution. The phosphate concentrations are 0.25% and 0.025%. 0.02 ml of Sr-85 or Rb-83 is added. After one hour of equilibration 1 ml fractions are pipetted. The activity in each fraction is measured and the $K_D$ calculated.

The $SnO_2$ (hydrated) used in Example 3 is sold by Applied Research Rue Hercoliers Brussels, Belgium as oxide d'etain hydrate, (which is French for hydrated tin oxide); OXTAIN (Trademark). This material is a chromatographic amorphous mixture comprising tin oxide and a substantial amount of hydrated stannic oxide. Upon heating, this material looses most of its Sr-Rb separation ability. Thus, there is a loss of activity with the loss of hydration of tin oxide.

| Example | Adsorbents | | pH | $K_D$ Sr-82 | $K_D$ Rb-82 |
|---|---|---|---|---|---|
| 1 | $Ti(OH)_4$ | saline (0.9%) | 8 | 40,000 | 52 |
| | | saline + 0.025% $PO_4^{-3}$ | 7.8 | 57,000 | 54 |
| | | saline + 0.25% $PO_4^{-3}$ | 8 | 71,000 | 56 |
| 2 | poly- | saline (0.9%) | 2.7 | 47,500 | <3 |
| | antimonic | saline 0.025% $PO_4^{-3}$ | 2.7 | 114,000 | <3 |
| | acid | saline + 0x.25% $PO_4^{-3}$ | 4.6 | 64,000 | <3 |
| 3 | $SnO_2$ | saline (0.9%) | 7.6 | 60,000 | <3 |
| | (hy- | saline + 0.025% $PO_4^{-3}$ | 7.6 | 41,000 | <3 |
| | drated) | saline + 0.25% $PO_4^{-3}$ | 7.6 | 42,000 | <3 |
| 4 | $Fe_2O_3$ | saline (0.9%) | 3.6 | <3 | <3 |
| | (hy- | saline + 0.025% $PO_4^{-3}$ | 4.1 | 7 | <3 |
| | drated) | saline + 0.25% $PO_4^{-3}$ | 6.5 | 1.182 | <3 |

In Examples 1-4 the difference in $K_D$ values for $^{82}Sr$ and $^{82}Rb$ shows the amount of separation. The high $K_D$ values for $^{82}Sr$ and the low $K_D$ values for $^{82}Rb$ show that $^{82}Sr$ is strongly adsorbed while $^{82}Rb$ is only slightly adsorbed. Thus, while a Sr loaded column of the adsorbants in Examples 1-4 is eluted with Sr remains adsorbed strongly with very minute breakthrough into the eluate. The daughter $^{82}Rb$ is only slightly adsorbed and passes out with the eluate in yields of about 90%.

The bolus volume is the amount of eluant needed to elute the available $^{82}Rb$.

EXAMPLE 5

Into a column 2 inches long and one fourth inch in diameter is placed 1.5 cc of $SnO_2$ particles having diameters of from 0.05 to 0.1 mm. Pre-equilibrium is done by washing the $SnO_2$ (hydrated) with saline three times. 2 ml of Sr-82 in saline solution having a pH of about 11 is loaded onto the $SnO_2$ (hydrated) particles by gravity in about one minute. The column is eluted at 12 ml per minute. The multi scaler mode on a multi channel analyzer was used to determine the elution profile. The bolus volume is about 3.4 ml.

The column is allowed to equilibrate and then counted for 777 KeV(Rb-82) with a Ge(Li) detector.

Table 1 shows the eluant composition volumes and the breakthrough fraction of $^{82}Sr$ for each volume eluted.

Table 2 shows a Summary of Characteristics of $^{82}Rb$ Generator System using inorganic adsorbers. At the bottom of the table are shown the characteristics of the $SnO_2$ (hydrated) adsorbent of the present invention.

TABLE 1

BREAKTHROUGH OF $^{82}Sr$ IN A $^{82}Rb$ GENERATOR HAVING A $SnO_2$ (HYDRATED) ADSORBENT

| Eluant | Volume (CC) | pH Eluate | Fraction of Sr loaded/cc |
|---|---|---|---|
| NaCl pH9 | 0-150 | ~1 | — |
| " | 150-160 | 1.5 | $7 \times 10^{-6}$ |
| " | 160-170 | 2 | $5 \times 10^{-6}$ |
| " | 170-200 | 2 | $7 \times 10^{-6}$ |
| $Na_2HPO_4$ | | | |
| 0.25% | 200-205 | 6.5 | $2 \times 10^{-6}$ |
| " | 210-250 | 7 | $1.5 \times 10^{-7}$ |
| $Na_2HPO_4$ | | | |
| 0.025% | 250-295 | 7 | $9 \times 10^{-8}$ |
| pH9 | 295-348 | 7 | $7 \times 10^{-8}$ |
| " | 345-600 | 7 | $5 \times 10^{-8}$ |
| " | 600-650 | 7 | $10^{-8}$ |
| " | 650-700 | 7 | $2 \times 10^{-8}$ |
| " | 700-750 | 7 | $2 \times 10^{-8}$ |
| " | 750-800 | 7 | $5 \times 10^{-9}$ |
| " | 800-850 | 7 | $\leqq 5 \times 10^{-9}$ |
| " | 850-900 | 7 | $\leqq 10^{-8}$ |
| " | 900-950 | 7 | $\leqq 1.5 \times 10^{-8}$ |
| " | 950-1000 | 7 | $\leqq 10^{-8}$ |
| " | 1000-1050 | 7 | $\leqq 2.5 \times 10^{-8}$ |
| " | 1050-1100 | 7 | $\leqq 10^{-8}$ |
| " | 1100-1150 | 7 | $\leqq 2 \times 10^{-8}$ |
| " | 1150-1200 | 7 | $\leqq 2.5 \times 10^{-8}$ |
| " | 1200-1250 | 7 | $\leqq 5 \times 10^{-9}$ |
| " | 1250-1300 | 7 | $\leqq 2.5 \times 10^{-8}$ |
| " | 1300-1350 | 7 | $\leqq 3 \times 10^{-8}$ |
| " | 1350-1400 | 7 | $\leqq 5 \times 10^{-9}$ |
| " | 1400-1450 | 7 | $\leqq 1.5 \times 10^{-8}$ |
| " | 1450-1800 | 7 | $\leqq 5 \times 10^{-9}$ |
| " | 1500-1550 | 7 | $\leqq 10^{-8}$ |
| " | 1550-1600 | 7 | $\leqq 1.5 \times 10^{-8}$ |
| " | 1600-2100 | 7.4 | $\leqq 10^{-8}$ |
| " | 2100-3100 | 7.4 | $\leqq 5 \times 10^{-10}$ |
| " | 3100-3925 | | |
| " | 3925-4600 | 7.4 | $1 \times 10^{-9}$ |
| " | 4600-5000 | 7.4 | $1 \times 10^{-9}$ |

In Table I above a "≦" represents less than or equal to

TABLE 2

SUMMARY OF CHARACTERISTICS OF $^{82}Rb$ GENERATOR SYSTEMS USING INORGANIC ADSORBERS

| Adsorbent | Column Size (ml) | Eluant Used | Elution Speed (ml/sec) | Eluate pH | Rb-82 Yield % | Sr-82 Breakthrough (ml) | No. Elutions Tested |
|---|---|---|---|---|---|---|---|
| $Al_2O_3$ | 1 | NaCl 2% | 1.2 | 8-9 | 70/10 ml | $4 \times 10^{-6}$ | 250 |

TABLE 2-continued

SUMMARY OF CHARACTERISTICS OF $^{82}Rb$ GENERATOR SYSTEMS USING INORGANIC ADSORBERS

| Adsorbent | Column Size (ml) | Eluant Used | Elution Speed (ml/sec) | Eluate pH | Rb-82 Yield % | Sr-82 Break-through (ml) | No. Elutions Tested |
|---|---|---|---|---|---|---|---|
| | | NaCl 0.9% | 1.2 | 8-9 | 25/10 ml | $5 \times 10^{-6}$ | 250 |
| $Al_2O_3$ | 2.25 | NaCl 2% | 0.5 | 8-9 | 76/20 ml | $5 \times 10^{-6} - 5 \times 10^{-8}$ | 300 |
| $Al_2O_3$ | 2.75 | NaCl 0.9% | 5 | 7.5 | 35/20 ml | — | 600 |
| | 2.75 | NaCl 0.9% | 0.1 | 7.5 | — | $1 \times 10^{-7}$ | 600 |
| $ZrO_2$ | 2.75 | NaCl 0.9% | 5 | 7.5 | 56/20 ml | — | 600 |
| | 2.75 | NaCl 0.9% | 0.1 | 7.5 | — | $2 \times 10^{-7}$ | 600 |
| $SnO_2$(hydrated) (of the present invention) | 1.5 | $PO_4^{-3}$ buffered isotonic saline (pH9) | 0.2 | 7.4 | 95/4 ml | $\leqq 5 \times 10^{-9}$ | 1,000 |

I claim:

1. A composition comprising $^{82}Sr$ and an adsorbant selected from the group consisting of tin oxide, hydrated tin oxide, polyantimonic acid, titanium oxide, ferric oxide, hydrated ferric oxide and hydrated titanium oxide.

2. The composition of claim 1 wherein said adsorbant is selected from the group consisting of hydrated tin oxide and polyantimonic acid.

3. The composition of claim 1 wherein said adsorbant comprises chromatotographic particles, said particles comprising hydrated tin oxide.

4. The composition of claim 3 wherein said $^{82}Sr$ is adsorbed on said adsorbant chromatographic particles, said particles having an average diameter of 0.01 to 0.9 mm.

5. Apparatus for generating $^{82}Rb$ comprising container means and the composition of claim 4 contained within said container means, said particles having an average diameter of 0.05 to 0.1 mm.

6. A low $^{82}Sr$ breakthrough method of generating $^{82}Rb$ from a $^{82}Sr$ charged adsorbant comprising eluting the $^{82}Rb$ from said adsorbant with an eluant solution wherein said adsorbant is selected from the group consisting of tin oxide, hydrated tin oxide, polyantimonic acid, hydrated titanium oxide, and hydrated ferric oxide.

7. The method of claim 6 wherein said adsorbant is selected from the group consisting of tin oxide, hydrated tin oxide, and polyantimonic acid.

8. The method of claim 7 further comprising providing container means and containing said $^{82}Sr$ charged adsorbant in said container means, said adsorbant comprising chromatographic particles having an average diameter of 0.01 to 0.9 mm.

9. The method of claim 8 wherein said eluant solution comprises isotonic saline.

10. The method of claim 9 wherein said eluant solution further comprises a pharmaceutically acceptable buffer.

11. The method of claim 10 wherein said buffer comprises a phosphate salt or a carbonate salt.

12. The composition of claim 3 wherein said hydrated tin oxide is a substantial amount of hydrated stannic oxide.

13. The composition of claim 12 further comprising tin oxide, said composition being amorphous.

* * * * *

UNITED STATES PATENT AND TRADEMARK OFFICE

CERTIFICATE EXTENDING PATENT TERM
UNDER 35 U.S.C. 156

| | | |
|---|---|---|
| Patent No. | : | 4,400,358 |
| Dated | : | August 23, 1983 |
| Inventor(s) | : | Rudi D. Neirinckx |
| Patent Owner | : | E.R. Squibb & Sons, Inc. |

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

2 YEARS with all rights pertaining thereto as provided by 35 USC 156 (b).

I have caused the seal of the Patent and Trademark Office to be affixed this 7th day of December 1990.

Harry F. Manbeck, Jr.
Assistant Secretary and Commissioner
of Patents and Trademarks